United States Patent [19]
Selbie et al.

[11] Patent Number: 5,571,695
[45] Date of Patent: Nov. 5, 1996

[54] HUMAN NEUROPEPTIDE Y-Y1 RECEPTOR

[75] Inventors: Lisa Selbie, McMahons Point; Herbert Herzog, New South Wales; John Shine, Woolwich, all of Australia

[73] Assignee: Garvan Institute of Medical Research, Darlinghurst, Australia

[21] Appl. No.: 232,144

[22] PCT Filed: Nov. 6, 1992

[86] PCT No.: PCT/AU92/00600
§ 371 Date: May 26, 1994
§ 102(e) Date: May 26, 1994

[87] PCT Pub. No.: WO93/09227
PCT Pub. Date: May 13, 1993

[30] Foreign Application Priority Data

Nov. 6, 1991 [AU] Australia ............................ PK 9336
Jun. 23, 1992 [AU] Australia ............................ PL 3131

[51] Int. Cl.⁶ ................................................. C12N 15/12
[52] U.S. Cl. ..................... 435/69.1; 435/70.1; 435/70.3; 536/23.1; 536/23.5
[58] Field of Search ................................. 435/69.1, 70.1, 435/70.3, 71.1, 71.2, 172.1, 240.1, 240.2, 243, 320.1; 536/23.1, 23.5

[56] References Cited

U.S. PATENT DOCUMENTS 4,332,892  6/1982  Ptashine et al. ........................ 435/68
4,743,679  5/1988  Cohen et al. ........................ 530/350

OTHER PUBLICATIONS

Sanders, *Animal Cell Biotechnology* vol. 4, 1990 pp. 16–69.
Wahlestedt et al, *Annals of N.Y. Academy Science* vol. 611, 1990, pp. 7–25.
Eva et al FEBS Lett 271 81–84 (1990).
Wahlestedt et al Life Science 50 pp 7–12 (1991).
Wahlesfedt et al Ann NY Acad Sci 611 7–26 (1990).
Minyish et al BBRC 175 1125–30 (1991).
Doarny et al Nature 347 72–75 (1990).
Sanders et al Animal Cell Biotech 4 16–70 (1990).
Kluxen et al PNAS 89 4618–4622 (1992).
Wallace et al Meth Enzymol 152 432–42 (1987).
Sasaki et al Nature 351 230–233 (1991).
Larhammer et al., *The Journal of Biological Chemistry*, vol. 267, No. 16, 5 Jun. 1992, pp. 10935–10938.
Herzog et al., *Proceedings of the National Academy of Sciences of the USA*, vol. 89, No. 13, 1 Jul. 1992, pp. 5794–5798.

*Primary Examiner*—Stephen G. Walsh
*Assistant Examiner*—Stephen Gucker
*Attorney, Agent, or Firm*—Rothwell, Figg, Ernst & Kurz

[57] ABSTRACT

The invention provides cDNA sequence and a genomic DNA sequence which encodes the human neuropeptide Y-Y1 receptor. These DNA sequences can be used to express the NPY-Y1 receptor in cells and can be sued to screen compounds for neuropeptide Y agonist and antagonist activity.

10 Claims, 6 Drawing Sheets

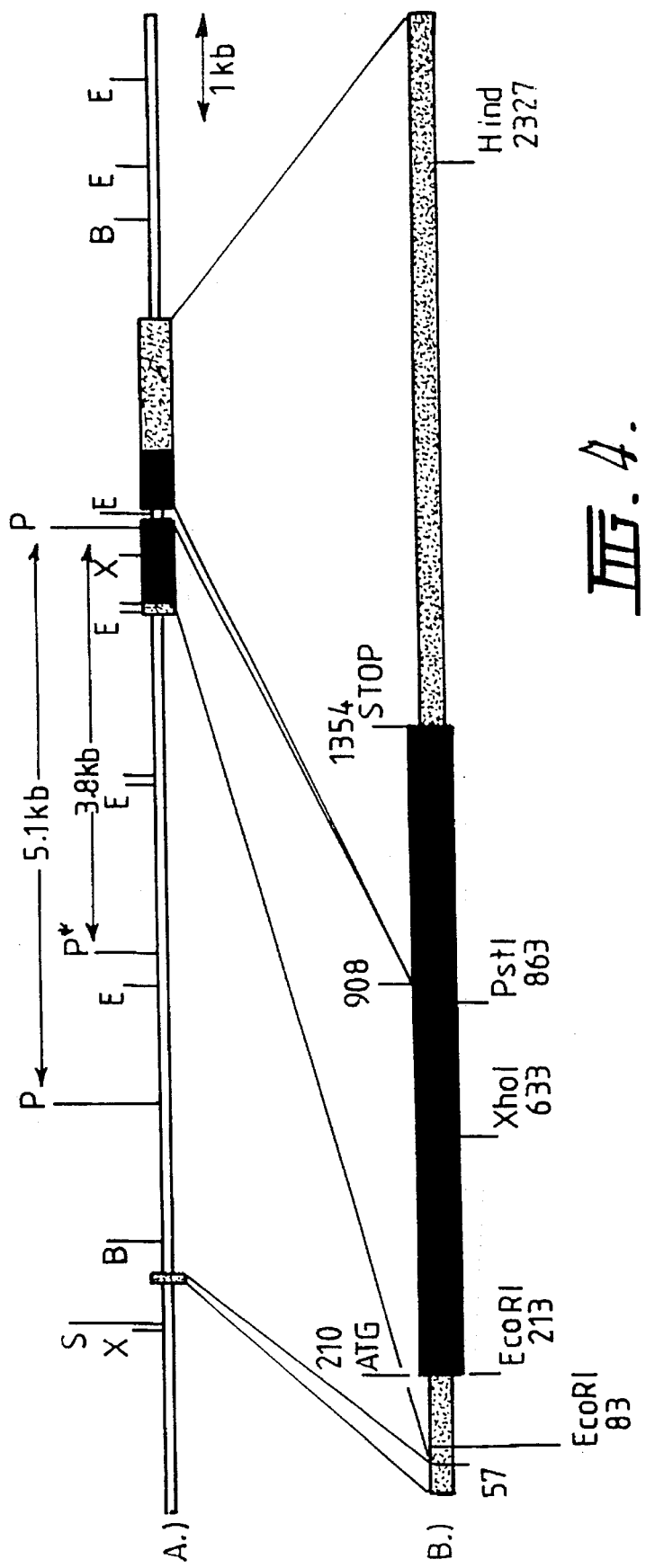

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:

(A) LENGTH: 30 base pairs
(B) TYPE: nucleic acid
(C) STRANDEDNESS: single
(D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:1:

| | | |
|---|---|---|
| CTGGTGCTGC AGTATTTTGG CCCACTCTGT | | 30 |

(2) INFORMATION FOR SEQ ID NO:2:

(i) SEQUENCE CHARACTERISTICS:
(A) LENGTH: 30 base pairs
(B) TYPE: nucleic acid
(C) STRANDEDNESS: single
(D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:2:

AATGTCTCAG AGAATTCTCC ATTTCTGGCC         30

(2) INFORMATION FOR SEQ ID NO:3:

(i) SEQUENCE CHARACTERISTICS:
(A) LENGTH: 2624 base pairs
(B) TYPE: nucleic acid
(C) STRANDEDNESS: single
(D) TOPOLOGY: linear (i i) MOLECULE TYPE: cDNA (i i i) HYPOTHETICAL: NO (i v) ANTI-SENSE: NO (i x) FEATURE:
(A) NAME/KEY: CDS
(B) LOCATION: 152..1306

(x i) SEQUENCE DESCRIPTION: SEQ ID NO:3:

| | | | | | | |
|---|---|---|---|---|---|---|
| ATTGTTCAGT | TCAAGGGAAT | GAAGAATTCA | GAATAATTTT | GGTAAATGGA | TTCCAATATC | 60 |
| GGGAATAAGA | ATAAGCTGAA | CAGTTGACCT | GCTTTGAAGA | AACATACTGT | CCATTTGTCT | 120 |
| AAAATAATCT | ATAACAACCA | AACCAATCAA | AATGAATTCA | ACATTATTTT | CCCAGGTTGA | 180 |
| AAATCATTCA | GTCCACTCTA | ATTTCTCAGA | GAAGAATGCC | CAGCTTCTGG | CTTTTGAAAA | 240 |
| TGATGATTGT | CATCTGCCCT | TGGCCATGAT | ATTTACCTTA | GCTCTTGCTT | ATGGAGCTGT | 300 |
| GATCATTCTT | GGTGTCTCTG | GAAACCTGGC | CTTGATCATA | ATCATCTTGA | AACAAAGGA | 360 |
| GATGAGAAAT | GTTACCAACA | TCCTGATTGT | GAACCTTTCC | TTCTCAGACT | TGCTTGTTGC | 420 |
| CATCATGTGT | CTCCCCTTTA | CATTTGTCTA | CACATTAATG | GACCACTGGG | TCTTTGGTGA | 480 |
| GGCGATGTGT | AAGTTGAATC | CTTTTGTGCA | ATGTGTTTCA | ATCACTGTGT | CCATTTCTC | 540 |
| TCTGGTTCTC | ATTGCTGTGG | AACGACATCA | GCTGATAATC | AACCCTCGAG | GGTGGAGACC | 600 |
| AAATAATAGA | CATGCTTATG | TAGGTATTGC | TGTGATTTGG | GTCCTTGCTG | TGGCTTCTTC | 660 |
| TTTGCCTTTC | CTGATCTACC | AAGTAATGAC | TGATGAGCCG | TTCCAAAATG | TAACACTTGA | 720 |
| TGCGTACAAA | GACAAATACG | TGTGCTTTGA | TCAATTTCCA | TCGGACTCTC | ATAGGTTGTC | 780 |

| | | | | | | |
|---|---|---|---|---|---|---|
| TTATACCACT | CTCCTCTTGG | TGCTGCAGTA | TTTTGGTCCA | CTTTGTTTTA | TATTTATTTG | 840 |
| CTACTTCAAG | ATATATATAC | GCCTAAAAAG | GAGAAACAAC | ATGATGGACA | AGATGAGAGA | 900 |
| CAATAAGTAC | AGGTCCAGTG | AAACCAAAAG | AATCAATATC | ATGCTGCTCT | CCATTGTGGT | 960 |
| AGCATTTGCA | GTCTGCTGGC | TCCCTCTTAC | CATCTTTAAC | ACTGTGTTTG | ATTGGAATCA | 1020 |
| TCAGATCATT | GCTACCTGCA | ACCACAATCT | GTTATTCCTG | CTCTGCCACC | TCACAGCAAT | 1080 |
| GATATCCACT | TGTGTCAACC | CCATATTTTA | TGGGTTCCTG | AACAAAAACT | TCCAGAGAGA | 1140 |
| CTTGCAGTTC | TTCTTCAACT | TTTGTGATTT | CCGGTCTCGG | GATGATGATT | ATGAAACAAT | 1200 |
| AGCCATGTCC | ACGATGCACA | CAGATGTTTC | CAAAACTTCT | TGAAGCAAG | CAAGCCCAGT | 1260 |
| CGCATTTAAA | AAAATCAACA | ACAATGATGA | TAATGAAAAA | ATCTGAAACT | ACTTATAGCC | 1320 |
| TATGGTCCCG | GATGACATCT | GTTAAAAAC | AAGCACAACC | TGCAACATAC | TTTGATTACC | 1380 |
| TGTTCTCCCA | AGGAATGGGG | TTGAAATCAT | TTGAAAATGA | CTAAGATTTT | CTTGTCTTGC | 1440 |
| TTTTTACTGC | TTTTGTTGTA | GTTGTCATAA | TTACATTTGG | AACAAAGGT | GTGGGCTTTG | 1500 |
| GGGTCTTCTG | GAAATAGTTT | TGACCAGACA | TCTTTGAAGT | GCTTTTTGTG | AATTTATGCA | 1560 |
| TATAATATAA | AGACTTTTAT | ACTGTACTTA | TTGGAATGAA | ATTTCTTTAA | AGTATTACGA | 1620 |
| TNNNCTGACT | TCAGAAGTAC | CTGCCATCCA | ATACGGTCAT | TAGATTGGGT | CATCTTGATT | 1680 |
| AGATTAGATT | AGATTAGATT | GTCAACAGAT | TGGGCCATCC | TTACTTTATG | ATAGGCATCA | 1740 |
| TTTTAGTGTG | TTACAATAGT | AACAGTATGC | AAAAGCAGCA | TTCAGGAGCC | GAAAGATAGT | 1800 |
| CTTGAAGTCA | TTCAGAAGTG | GTTTGAGGTT | TCTGTTTTTT | GGTGGTTTTT | GTTTGTTTTT | 1860 |
| TTTTTTTTTC | ACCTTAAGGG | AGGCTTTCAT | TTCCTCCCGA | CTGATTGTCA | CTTAAATCAA | 1920 |
| AATTTAAAAA | TGAATAAAAA | GACATACTTC | TCAGCTGCAA | ATATTATGGA | GAATTGGGCA | 1980 |
| CCCACAGGAA | TGAAGAGAGA | AAGCAGCTCC | CCAACTTCAA | AACCATTTTG | GTACCTGACA | 2040 |
| ACAAGAGCAT | TTTAGAGTAA | TTAATTTAAT | AAAGTAAATT | AGTATTGCTG | CAAATAGCTA | 2100 |
| AATTATATTT | ATTTGAATTG | ATGGTCAAGA | GATTTTCCAT | TTTTTTTACA | GACTGTTCAG | 2160 |
| TGTTTGTCAA | GCTTCTGGTC | TAATATGTAC | TCGAAAGACT | TTCCGCTTAC | AATTTGTAGA | 2220 |
| AACACAAATA | TCGTTTTCCA | TACAGCAGTG | CCTATATAGT | GACTGATTTT | AACTTTCAAT | 2280 |
| GTCCATCTTT | CAAAGGAAGT | AACACCAAGG | TACAATGTTA | AAGGAATATT | CACTTTACCT | 2340 |
| AGCAGGGAAA | AATACACAAA | AACTGCAGAT | ACTTCATATA | GCCCATTTTA | ACTTGTATAA | 2400 |
| ACTGTGTGAC | TTGTGGCGTC | TTATAAATAA | TGCACTGTAA | AGATTACTGA | ATAGTTGTGT | 2460 |
| CATGTTAATG | TGCCTAATTT | CATGTATCTT | GTAATCATGA | TTGAGCCTCA | GAATCATTTG | 2520 |
| GAGAAACTAT | ATTTTAAAGA | ACAAGACATA | CTTCAATGTA | TTATACAGAT | AAAGTATTAC | 2580 |
| ATGTGTTTGA | TTTTAAAAGG | GCGGACATTT | TATTAAAATC | AAGG | | 2624 |

( 2 ) INFORMATION FOR SEQ ID NO:4:

( i ) SEQUENCE CHARACTERISTICS:
        ( A ) LENGTH: 384 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

```
Met  Asn  Ser  Thr  Leu  Phe  Ser  Gln  Val  Glu  Asn  His  Ser  Val  His  Ser
 1              5                        10                         15

Asn  Phe  Ser  Glu  Lys  Asn  Ala  Gln  Leu  Leu  Ala  Phe  Glu  Asn  Asp  Asp
```

|  |  |  | 20 |  |  |  | 25 |  |  |  | 30 |  |  |
|---|---|---|---|---|---|---|---|---|---|---|---|---|---|
| Cys | His | Leu<br>35 | Pro | Leu | Ala | Met<br>40 | Ile | Phe | Thr | Leu | Ala<br>45 | Ala | Tyr | Gly |
| Ala | Val<br>50 | Ile | Ile | Leu | Gly<br>55 | Val | Ser | Gly | Asn | Leu<br>60 | Ala | Leu | Ile | Ile | Ile |
| Ile<br>65 | Leu | Lys | Gln | Lys | Glu<br>70 | Met | Arg | Asn | Val | Thr<br>75 | Asn | Ile | Leu | Ile | Val<br>80 |
| Asn | Leu | Ser | Phe | Ser<br>85 | Asp | Leu | Leu | Val | Ala<br>90 | Ile | Met | Cys | Leu | Pro<br>95 | Phe |
| Thr | Phe | Val<br>100 | Tyr | Thr | Leu | Met | Asp | His<br>105 | Trp | Val | Phe | Gly | Glu<br>110 | Ala | Met |
| Cys | Lys | Leu<br>115 | Asn | Pro | Phe | Val | Gln<br>120 | Cys | Val | Ser | Ile | Thr<br>125 | Val | Ser | Ile |
| Phe | Ser<br>130 | Leu | Val | Leu | Ile | Ala<br>135 | Val | Glu | Arg | His | Gln<br>140 | Leu | Ile | Ile | Asn |
| Pro<br>145 | Arg | Gly | Trp | Arg | Pro<br>150 | Asn | Asn | Arg | His | Ala<br>155 | Tyr | Val | Gly | Ile | Ala<br>160 |
| Val | Ile | Trp | Val | Leu<br>165 | Ala | Val | Ala | Ser | Ser<br>170 | Leu | Pro | Phe | Leu | Ile<br>175 | Tyr |
| Gln | Val | Met | Thr<br>180 | Asp | Glu | Pro | Phe | Gln<br>185 | Asn | Val | Thr | Leu | Asp<br>190 | Ala | Tyr |
| Lys | Asp | Lys<br>195 | Tyr | Val | Cys | Phe | Asp<br>200 | Gln | Phe | Pro | Ser | Asp<br>205 | Ser | His | Arg |
| Leu | Ser<br>210 | Tyr | Thr | Thr | Leu | Leu<br>215 | Leu | Val | Leu | Gln | Tyr<br>220 | Phe | Gly | Pro | Leu |
| Cys<br>225 | Phe | Ile | Phe | Ile | Cys<br>230 | Tyr | Phe | Lys | Ile | Tyr<br>235 | Ile | Arg | Leu | Lys | Arg<br>240 |
| Arg | Asn | Asn | Met | Met<br>245 | Asp | Lys | Met | Arg | Asp<br>250 | Asn | Lys | Tyr | Arg | Ser<br>255 | Ser |
| Glu | Thr | Lys | Arg<br>260 | Ile | Asn | Ile | Met | Leu<br>265 | Leu | Ser | Ile | Val | Val<br>270 | Ala | Phe |
| Ala | Val | Cys<br>275 | Trp | Leu | Pro | Leu | Thr<br>280 | Ile | Phe | Asn | Thr | Val<br>285 | Phe | Asp | Trp |
| Asn | His<br>290 | Gln | Ile | Ile | Ala | Thr<br>295 | Cys | Asn | His | Asn | Leu<br>300 | Leu | Phe | Leu | Leu |
| Cys<br>305 | His | Leu | Thr | Ala | Met<br>310 | Ile | Ser | Thr | Cys | Val<br>315 | Asn | Pro | Ile | Phe | Tyr<br>320 |
| Gly | Phe | Leu | Asn | Lys<br>325 | Asn | Phe | Gln | Arg | Asp<br>330 | Leu | Gln | Phe | Phe | Phe<br>335 | Asn |
| Phe | Cys | Asp | Phe<br>340 | Arg | Ser | Arg | Asp | Asp<br>345 | Asp | Tyr | Glu | Thr | Ile<br>350 | Ala | Met |
| Ser | Thr | Met<br>355 | His | Thr | Asp | Val | Ser<br>360 | Lys | Thr | Ser | Leu | Lys<br>365 | Gln | Ala | Ser |
| Pro | Val<br>370 | Ala | Phe | Lys | Lys | Ile<br>375 | Asn | Asn | Asn | Asp | Asp<br>380 | Asn | Glu | Lys | Ile |

( 2 ) INFORMATION FOR SEQ ID NO:5:

( i ) SEQUENCE CHARACTERISTICS:
        ( A ) LENGTH: 4571 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:

( A ) NAME/KEY: INTRON
( B ) LOCATION: 1604

( x i ) SEQUENCE DESCRIPTION: SEQ ID NO:5:

| | | | | | | |
|---|---|---|---|---|---|---|
| AACGTACTCG | TGTACATTCT | ATTTTTTTCT | TCATAATGTT | CAGTACTGTA | GTACTAATCA | 60 |
| CCGAGAAAAT | TGCATTGACT | CTTTTCGACC | ACCAGGGAAA | TATTCAGCTC | ATGGTTCTCC | 120 |
| CCAAAAAAAC | TAAAAAGCAG | CTAAGCGCTG | GGAACAAATC | TGACTTATTG | CATTTTCTCA | 180 |
| GTGGGCCAAA | GAAAGGAGGG | CCGATTGACT | GCTTTGACTT | TTTAAAGGTC | TTCTCTTTGT | 240 |
| TCACTTATAA | AGTGAGGAAA | ACAAATTCTC | GGCACTGGCG | TGAGAGTTGA | GCGTCACAAA | 300 |
| AGAAAGCAAA | AGAAAATATT | AGTGCCATTA | TTGTGGCGAA | TTTCATGTTT | CCCAGCGAGC | 360 |
| CCTTTGATTC | CTGGTTTGGG | CTGGCGCTCG | AGCTCTCCAG | CCGGGTATGA | CTTCGGCCAC | 420 |
| AAGATGGCAC | TGACCTGCAA | ACAAGAAAA | GCACAGTGGC | ACCGACTTTT | TCAAGCCTCG | 480 |
| GGAAACTGCC | CTGCCTTCCC | CGGAGTCGAG | GACTGTGGGG | ATTAGGGCTT | CCTTTCCCCT | 540 |
| GCGCGGGAGG | TCTGTGTCGA | ATAATGTGTG | GCTTCTGTTG | GATTGCTTTT | CTTTCCAAAA | 600 |
| TTCCTAGGCA | ATGCTTCCCC | GAGGTGTGCA | CCTTTGTGAG | GTGTTTGTGG | GGTTGGGGGA | 660 |
| GCTTCAGGCG | CTACTCGCGG | GACGACGTCA | CGTGATCCGG | GATGAGGTGG | AGTTCGGCTT | 720 |
| TAAGGAGGCG | TCTCTTCCTA | GCTTCATCAA | TCTTTAGGAT | CTGAGCAGGA | GAAATACCAG | 780 |
| CGGATCTTCC | CCACTCTGCT | CCCTTCCATT | CCCACCCTTC | CTTCTTTAAT | AAGCAGGAGC | 840 |
| GAAAAGACA | AATTCCAAAG | AGGGTAAGTT | GCGAGTTTAT | GCCTTTCCAG | AGACTTCTGC | 900 |
| GAAATCTCTC | ATTGACAAGG | TGAAGGATGA | GAGGGAAGA | AAAACGATGC | GAGTGTCCGA | 960 |
| AACTGGCTCT | GGGGGACCAA | GGTGGGGTCT | CCAGTGCAGG | CAGGTCGCAG | GTTGCTCCAA | 1020 |
| ATCACCGGAC | CGTTCGCGGG | CTCCTGCCGA | AGGGTATGGG | GACGACGCGG | GTGAAAGGAG | 1080 |
| AGGGTACCCT | ACGCGGAGTT | CGGGCTTTCC | CCCCACCTGC | TCCCGGGGAA | TTTCTGGATG | 1140 |
| GGGATCCAAG | TTTTCCTTTA | CCCCGGTTCT | CTTTAAAAGG | CCGAGGCACT | GGGAAGGCGC | 1200 |
| CCGAGTTCGC | CTATCCCACA | CCCGCTCATT | TTCCTTACGT | GTCTTGAGCT | GGCTGGAGGC | 1260 |
| ACTGGCTCTG | GCCGCACCGG | AGTTTTCGCG | GAGTAACTGG | CTGGGATGAG | CCGGAGAAGG | 1320 |
| GTGGGCTTGC | ACGTCGCCCA | GCGTCGCACG | GGTCCGCGGC | AGGTGTCGGG | CTGGGAGCTG | 1380 |
| GCGGAGGTGG | GAGTAGCCCT | CGGCGCGGAC | CCCAGCGCGC | AAGCCCACCC | CCACTTGCGG | 1440 |
| GTTCCGCGCT | TCTCGGCTGC | AATCGAGCCG | CGCACCGCAG | TACCGGGCGC | TTCGAGTGTG | 1500 |
| GCGCTGCGCC | CCGATAGACA | CCCGAAGCTT | TTAATCATCG | GAGTTCTAAT | CAGGGTTCTC | 1560 |
| TTTAGCTCTT | TCTTTTAGAA | AAGTAATGAT | GGAACGTGGC | TGGTATTCCT | TACTAACTTA | 1620 |
| TAGACCATTA | TGTTTACTA | AGACTTGTTC | TGTAAGCAAG | TCCAATTAAA | AATTTTATTT | 1680 |
| TTTCTTTATT | CAGTATGTTT | TCACCATTTC | TGCTATTTTA | GAAAGATGTT | TACAAGATTA | 1740 |
| CATTTGTTT | ATTTATTTCA | GTGTTTTCAC | TTTAAAGAGT | TCTGTGAGTC | AGAAGTCATT | 1800 |
| TTGACTGCCC | TCAATAAAAT | TAGTAATGCA | ATTGGTCATT | TTCTCTTTAC | AGATTGTTCA | 1860 |
| GTTCAAGGGA | ATGAAGAATT | CAGAATAATT | TTGGTAAATG | GATTCCAATA | TCGGGAATAA | 1920 |
| GAATAAGCTG | AACAGTTGAC | CTGCTTTGAA | GAAACATACT | GTCCATTTGT | CTAAAATAAT | 1980 |
| CTATAACAAC | CAAACCAATC | AAAATGAATT | CAACATTATT | TTCCCAGGTT | GAAAATCATT | 2040 |
| CAGTCCACTC | TAATTTCTCA | GAGAAGAATG | CCCAGCTTCT | GGCTTTTGAA | AATGATGATT | 2100 |
| GTCATCTGCC | CTTGGCCATG | ATATTTACCT | TAGCTCTTGC | TTATGGAGCT | GTGATCATTC | 2160 |
| TTGGTGTCTC | TGGAAACCTG | GCCTTGATCA | TAATCATCTT | GAAACAAAAG | GAGATGAGAA | 2220 |
| ATGTTACCAA | CATCCTGATT | GTGAACCTTT | CCTTCTCAGA | CTTGCTTGTT | GCCATCATGT | 2280 |

```
GTCTCCCCTT TACATTTGTC TACACATTAA TGGACCACTG GGTCTTTGGT GAGGCGATGT    2340
GTAAGTTGAA TCCTTTTGTG CAATGTGTTT CAATCACTGT GTCCATTTTC TCTCTGGTTC    2400
TCATTGCTGT GGAACGACAT CAGCTGATAA TCAACCCTCG AGGGTGGAGA CCAAATAATA    2460
GACATGCTTA TGTAGGTATT GCTGTGATTT GGGTCCTTGC TGTGGCTTCT TCTTTGCCTT    2520
TCCTGATCTA CCAAGTAATG ACTGATGAGC CGTTCCAAAA TGTAACACTT GATGCGTACA    2580
AAGACAAATA CGTGTGCTTT GATCAATTTC CATCGGACTC TCATAGGTTG TCTTATACCA    2640
CTCTCCTCTT GGTGCTGCAG TATTTTGGTC CACTTTGTTT TATATTTATT TGCTACTTCA    2700
AGGTAAGAAA ACTTTTTTTC TATCATTTCC ATTTTTACCT TCTTTACACA GAATTCCTCA    2760
TCAAATGAGT GTTTCTATTT AAACTTTTTT CTTCCATAGA TATATATACG CCTAAAAGG    2820
AGAAACAACA TGATGGACAA GATGAGAGAC AATAAGTACA GGTCCAGTGA AACCAAAGA    2880
ATCAATATCA TGCTGCTCTC CATTGTGGTA GCATTTGCAG TCTGCTGGCT CCCTCTTACC    2940
ATCTTTAACA CTGTGTTTGA TTGGAATCAT CAGATCATTG CTACCTGCAA CCACAATCTG    3000
TTATTCCTGC TCTGCCACCT CACAGCAATG ATATCCACTT GTGTCAACCC CATATTTTAT    3060
GGGTTCCTGA ACAAAAACTT CCAGAGAGAC TTGCAGTTCT TCTTCAACTT TTGTGATTTC    3120
CGGTCTCGGG ATGATGATTA TGAAACAATA GCCATGTCCA CGATGCACAC AGATGTTTCC    3180
AAAACTTCTT TGAAGCAAGC AAGCCCAGTC GCATTTAAAA AAATCAACAA CAATGATGAT    3240
AATGAAAAAA TCTGAAACTA CTTATAGCCT ATGGTCCGG ATGACATCTG TTTAAAAACA    3300
AGCACAACCT GCAACATACT TTGATTACCT GTTCTCCCAA GGAATGGGGT TGAAATCATT    3360
TGAAAATGAC TAAGATTTTC TTGTCTTGCT TTTTACTGCT TTTGTTGTAG TTGTCATAAT    3420
TACATTTGGA ACAAAGGTG TGGGCTTTGG GGTCTTCTGG AAATAGTTTT GACCAGACAT    3480
CTTTGAAGTG CTTTTTGTGA ATTTATGCAT ATAATATAAA GACTTTTATA CTGTACTTAT    3540
TGGAATGAAA TTTCTTTAAA GTATTACGAT NNNCTGACTT CAGAAGTACC TGCCATCCAA    3600
TACGGTCATT AGATTGGGTC ATCTTGATTA GATTAGATTA GATTAGATTG TCAACAGATT    3660
GGGCCATCCT TACTTTATGA TAGGCATCAT TTAGTGTGT TACAATAGTA ACAGTATGCA    3720
AAAGCAGCAT TCAGGAGCCG AAAGATAGTC TTGAAGTCAT TCAGAAGTGG TTTGAGGTTT    3780
CTGTTTTTTG GTGGTTTTG TTTGTTTTTT TTTTTTTCA CCTTAAGGGA GGCTTTCATT    3840
TCCTCCCGAC TGATTGTCAC TTAAATCAAA ATTTAAAAAT GAATAAAAAG ACATACTTCT    3900
CAGCTGCAAA TATTATGGAG AATTGGGCAC CCACAGGAAT GAAGAGAGAA AGCAGCTCCC    3960
CAACTTCAAA ACCATTTTGG TACCTGACAA CAAGAGCATT TTAGAGTAAT TAATTTAATA    4020
AAGTAAATTA GTATTGCTGC AAATAGCTAA ATTATATTTA TTTGAATTGA TGGTCAAGAG    4080
ATTTTCCATT TTTTTTACAG ACTGTTCAGT GTTTGTCAAG CTTCTGGTCT AATATGTACT    4140
CGAAAGACTT TCCGCTTACA ATTTGTAGAA ACACAAATAT CGTTTTCCAT ACAGCAGTGC    4200
CTATATAGTG ACTGATTTTA ACTTAATGTC CATCTTTCAA AGGAAGTAAC ACCAAGGTAC    4260
AATGTTAAAG GAATATTCAC TTTACCTAGC AGGGAAAAAT ACACAAAAAC TGCAGATACT    4320
TCATATAGCC CATTTTAACT TGTATAAACT GTGTGACTTG TGGCGTCTTA TAAATAATGC    4380
ACTGTAAAGA TTACTGAATA GTTGTGTCAT GTTAATGTGC CTAATTTCAT GTATCTTGTA    4440
ATCATGATTG AGCCTCAGAA TCATTTGGAG AAACTATATT TTAAGAACA AGACATACTT    4500
CAATGTATTA TACAGATAAA GTATTACATG TGTTTGATTT TAAAGGGCG GACATTTTAT    4560
TAAAATCAAG G                                                        4571
```

( 2 ) INFORMATION FOR SEQ ID NO:6:

( i ) SEQUENCE CHARACTERISTICS:
        ( A ) LENGTH: 6 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:6:

C C A T T C       6

( 2 ) INFORMATION FOR SEQ ID NO:7:

( i ) SEQUENCE CHARACTERISTICS:
        ( A ) LENGTH: 6 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:7:

A A A T A C       6

( 2 ) INFORMATION FOR SEQ ID NO:8:

( i ) SEQUENCE CHARACTERISTICS:
        ( A ) LENGTH: 7 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:8:

T C A A T C T       7

( 2 ) INFORMATION FOR SEQ ID NO:9:

( i ) SEQUENCE CHARACTERISTICS:
        ( A ) LENGTH: 8 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:9:

C G A C G T C A       8

( 2 ) INFORMATION FOR SEQ ID NO:10:

( i ) SEQUENCE CHARACTERISTICS:
        ( A ) LENGTH: 8 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO (xi) SEQUENCE DESCRIPTION: SEQ ID NO:10:

GCGAGCCC  8

(2) INFORMATION FOR SEQ ID NO:11:

(i) SEQUENCE CHARACTERISTICS:
(A) LENGTH: 6 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (xi) SEQUENCE DESCRIPTION: SEQ ID NO:11:

ATTAAA  6

(2) INFORMATION FOR SEQ ID NO:12:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (iii) HYPOTHETICAL: NO (xi) SEQUENCE DESCRIPTION: SEQ ID NO:12:

Ser  Ala  Leu  Arg  His  Tyr
1                 5

HUMAN NEUROPEPTIDE Y-Y1 RECEPTOR

This application is a national stage filed under 35 USC 371 of PCT/AU92/00600 filed Nov. 6, 1991.

FIELD OF THE INVENTION

The present invention relates to cDNA and genomic DNA sequences which encode the human neuropeptide Y-Y1 receptor. In addition the present invention relates to the use of these sequences in the production of the human neuropeptide Y-Y1 receptor and related receptor subtypes using recombinant DNA technology and to methods of screening and testing compounds for neuropeptide Y (NPY) agonist or antagonist activity.

BACKGROUND OF THE INVENTION

Neuropeptide Y (NPY) has a wide range of functions in the body, particularly affecting the cardiovascular system. Within the peripheral nervous system NPY is present in postganglionic sympathetic nerves, being co-localised and co-released with other neurotransmitter, including catecholamines. When used pharmacologically, NPY has been shown to have a potent vasoconstrictor activity as well as dramatically potentiating the vasoconstriction caused by many other pressor agents. Particularly high concentrations of NPY are found in the sympathetic nerves supplying the coronary, cerebral and renal vasculature and when infused into these vascular beds, NPY causes prolonged vasoconstriction that is not reversed by adrenergic blocking agents. These observations have led to the proposal that NPY is the candidate transmitter for pathological vasospasm, a major cause of morbidity and mortality when involving the coronary and cerebral vessels.

NPY also appears to be involved in interaction with the renin angiotensin system. NPY containing sympathetic nerve terminals are found on the juxta-glomerular apparatus of the renal cortex and NPY influences renin release. These data, together with the demonstration of alterations in NPY concentrations in hypertensive animal models and the pressor response to infusion of the peptide, have resulted in implications of this peptide in hypertension.

Within the central nervous system NPY is localised predominantly within interneurons where it appears to have a regulatory role. It therefore has widespread and diverse effects including effects on memory and a possible role in Alzheimer's disease. NPY is the most potent known substance to cause an increase in feeding and may play a role in the genetic basis of Type II diabetes mellitus. NPY may also play a role as a regulatory agent in pituitary function as well as potential neuromodulatory function in stress responses and in reproductive function.

Specific agonists and antagonists of NPY are therefore likely to be of substantial benefit for therapy of a wide range of clinical disorders. As NPY possess a compact tertiary structure and different parts of the molecule are required for interaction with different subtypes of the receptor, the logical development of both agonists and antagonists is critically dependent upon the availability and knowledge of specific receptor structure.

NPY binds specifically to at least two receptors, Y1 and Y2. (Fuhlendorff, J., et al., Proc. Natl. Acad. Sci. U.S.A. 87:182–186, 1990). In addition, a third receptor subtype has been suggested (Wahlstedt, et al, Life Sciences 50:PL7–PL12, 1991; Michel, MC Trends in Pharmacol. Sci. 12:389–394, 1991). While it has been demonstrated that NPY receptors couple to the adenylate cyclase second messenger system, it remains probable that additional NPY receptor subtypes exist since there is evidence that phosphatidylinositol turnover, cations, and arachidonic acid may also function ask second messengers for NPY. Since NPY agonists and antagonists may have commercial value as potential anti-hypertensive agents, cardiovascular drugs, neuronal growth factors, anti-psychotics, anti-obesity and anti-diabetic agents, the ability to produce NPY receptors by recombinant DNA technology would be advantageous.

The present invention have isolated full length cDNA clones encoding the human Y1 NPY receptor (designated Y1) from human hippocampal cDNA using DNA homology screening. The receptor sequences were identified as the human Y1NPY receptor by expression of the cloned cDNA in mammalian cells and by measurement of specific binding to the transfected cells by a variety of NPY analogues. The receptor has also been shown to couple to both the inhibition of adenylate cyclase activity and increases in intracellular cytosolic calcium levels. In addition, the receptor has been expressed in a bacterial cells, allowing for additional drug screening methods as well as purification of the receptor protein. The DNA sequences represent a novel human receptor which may be of clinical and commercial importance.

SUMMARY OF THE INVENTION

Accordingly, in a first aspect the present invention consists in a cDNA molecule encoding the human NPY-Y1 receptor, the cDNA molecule having a sequence substantial as shown in Table 1 or a functionally equivalent sequence.

In a second aspect the present invention consists in a genomic DNA molecule encoding the human NPY-Y1 receptor, the genomic DNA molecule having a sequence substantially as shown in Table 2 or a functionally equivalent sequence.

As used herein the term "functionally equivalent sequence" is intended to cover minor variation in the DNA sequence which, due to degenerancy in the DNA code, do not result in the sequence encoding a different polypeptide. Further, this term is intended to cover alterations in the DNA code which lead to changes in the encoded polypeptide, but in which such changes do not affect the biological activity of the peptide. In addition, this term is intended to cover use of the human NPY Y1 receptor gene or gene fragments for expression in cell lines to be used in drug screening.

In a third aspect the present invention consists in a method of producing human NPY-Y1 receptors comprising culturing a cell transformed with the cDNA molecule of the first aspect of the present invention or the genomic DNA molecule of the second aspect of the present invention under conditions which allow expression of the DNA sequence and optionally recovering the human NPY-Y1 receptor.

Where the cDNA sequence is used the cells may be either mammalian cells or bacterial cells. Where the cells are mammalian cells it is presently preferred that the cells are Chinese Hamster Ovary (CHO) cells or human embryonic kidney 293 cells.

It will also be clear to persons skilled in the art that where genomic DNA sequence is used that gene fragments could be used to obtain expression of the NPY-Y1 receptor. It is intended that the use of such gene fragments is included within the scope of the present invention.

In a further preferred embodiment the cDNA molecule is under the control of the CMV promoter when expressed in mammalian cells.

In a fourth aspect the present invention consists in a method of screening compounds for NPY agonist or antagonist activity, comprising contacting the molecule with the human NPY-Y1 receptor produced by the method of the second aspect of the present invention.

In a preferred embodiment of the present invention the NPY-Y1 receptor is present on the surface of a cell, preferably CHO or 293 cells or bacterial cells.

The cDNA and genomic DNA molecules of the present invention represent novel human receptors. These receptors may be of interest both clinically and commercially as they are expressed in many regions of the body and a NPY affects a wide number of systems.

By using the cDNA or genomic DNA sequences of the present invention it is possible to isolate the neuropeptide Y-Y1 receptor protein in a substantially pure form.

Accordingly, in a fifth aspect the present invention consists in neuropeptide Y-Y1 receptor in a substantially pure form.

It is believed that sequence of the present invention will also enable the isolation of DNA sequences encoding other NPY-Y1 receptor subtypes including the NPY-Y2 and NPY-Y3 receptor, by using the proof in DNA homology screening of DNA libraries of interest.

In order that the nature of the present invention may be more clearly understood preferred forms thereof will now be described with reference to the following examples and drawings in which:

BRIEF DESCRIPTION OF THE DRAWINGS

FIG. 4 shows the restriction map for SacI, XhoI, BamHI and EcoRI of λC clone.

METHODS

Isolation of cDNA

Figure 1:
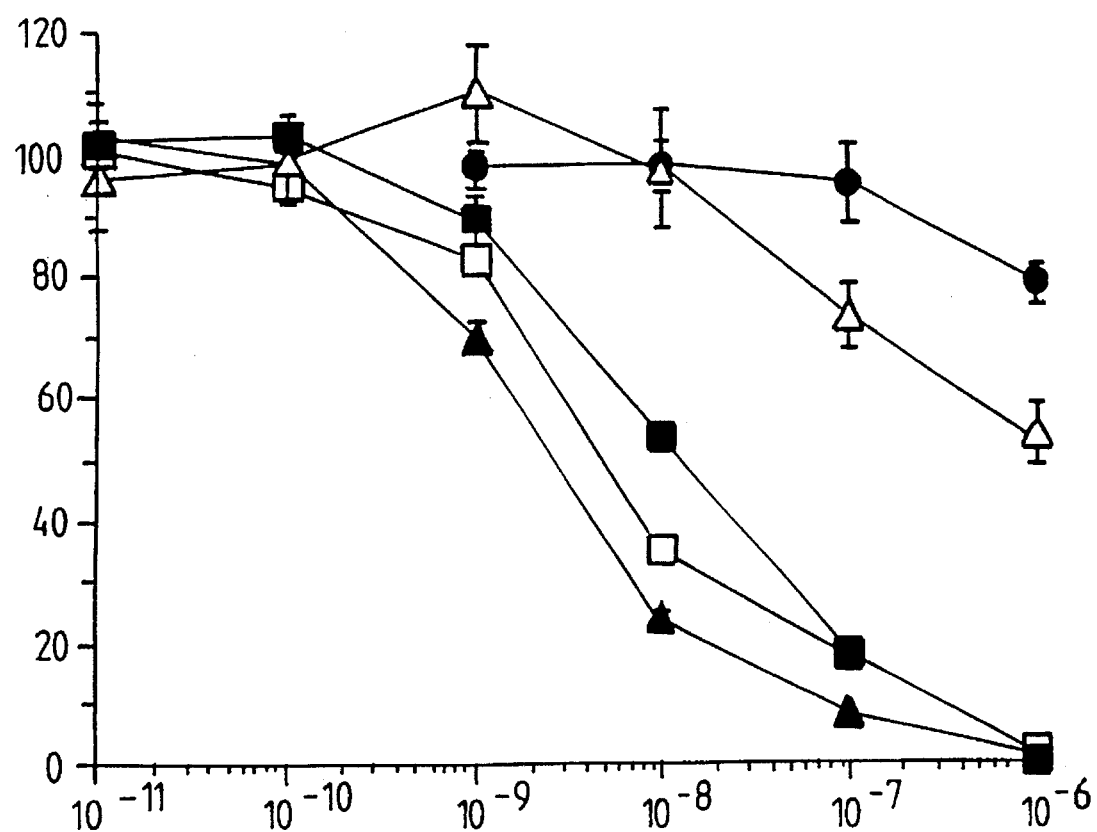
FIG. 1 shows inhibition of porcine [$^{125}$I]-PYY binding with various NPY-related peptides. Increasing concentrations of human NPY [□], human [$L^{31},P^{34}$]NPY[■], porcine peptide YY [▲], peptide YY residues 13–36 [●], and human pancreatic polypeptide [△] were tested for their ability to inhibit the binding of [$^{125}$I]-PYY. Results were expressed as a percentage of the maximal specifically bound radiolabelled PYY. Standard errors of triplicate samples are shown. Untransfected CHO cells showed no specific binding of NPY.

Total RNA (3 μg) from rat brain was used as a template to synthesize random primed single-stranded cDNAs. These cDNAs were used in a polymerase chain reaction (PCR) together with the oligonucleotide primers R1 (CTG GTG CTG CAG TAT TTT GGC CCA CTC TGT) (SEQ ID NO:1) and R2 (AAT GTC TCA GAG AAT TCT CCA TTT CTG GCC) (SEQ ID NO:2) 30 pmol each) which correspond to position 672-584 and 48-78 in the rat cDNA clone FC5R, respectively. PCR condition: 30 cycles at 95 for 1 min, 63 C for 2 min and 72 C for 1 min. The reaction product was digested with EcoR I and Pst I, gel purified and subcloned for sequencing into the Bluescript vector (Stratagene) to show authenticity.

Two lambda cDNA libraries derived from human fetal brain (Clonetec) and human adult hippocampus (Stratagene) (9.10$^5$ pfu each) were screened with the rat cDNA as a probe under following hybridization conditions: 5×SSPE, 0.1% SDS and 5× Denhardt at 60 C for 16 hours. The filters were washed twice with 2×SSC and 0.1% SDS at 60 C for 15 min. Three strongly hybridizing clones were isolated and the cDNA inserts were subcloned for sequencing into Bluescript vectors. The largest cDNA (2.5 kb) contains an open reading frame for 384 amino acids encoding the human NPY receptor subtype Y$_1$ (Table 1). The two other clones (F5 and F13) are truncated versions of the same cDNA with 100% identify in the overlapping region (position 664-1555 and 670-1925) respectively.

The mammalian expression construct pN-H(3–4) was made by subcloning a PCR fragment containing only the coding region of the NPY Y$_1$ receptor into the pcDNA NEO vector. The construct is under the control of the CMV promoter and contains the neomycin gene for selection.

The expression construct pN-H3 was transfected into the mammalian cell line CHO K1 using a modified calcium

TABLE 1

Human Neuropeptide Y Y1 receptor cDNA (SEQ ID NO: 3)

```
                                                                              70
     *         *         *         *         *         *         *
ATTGTTCAGTTCAAGGGAATGAAGAATTCAGAATAATTTTGGTAAATGGATTCCAATATCGGGAATAAGA

140
     *         *         *         *         *         *         *
ATAAGCTGAACAGTTGACCTGCTTTGAAGAAACATACTGTCCATTTGTCTAAAATAATCTATAACAACCA
```

TABLE 1-continued

Human Neuropeptide Y Y1 receptor cDNA (SEQ ID NO: 3)

```
                                                                    210
       *         *         *         *         *         *         *
AACCAATCAAAATGAATTCAACATTATTTTCCCAGGTTGAAAATCATTCAGTCCACTCTAATTTCTCAGA
              M  N  S  T  L  F  S  Q  V  E  N  H  S  V  H  S  N  F  S  E
                                                                    280
       *         *         *         *         *         *         *
GAAGAATGCCCAGCTTCTGGCTTTTGAAAATGATGATTGTCATCTGCCCTTGGCCATGATATTTACCTTA
  K  N  A  Q  L  L  A  F  E  N  D  D  C  H  L  P  L  A  M  I  F  T  L
                                                                    350
       *         *         *         *         *         *         *
GCTCTTGCTTATGGAGCTGTGATCATTCTTGGTGTCTCTGGAAACCTGGCCTTGATCATAATCATCTTGA
  A  L  A  Y  A  A  V  I  I  L  G  V  S  G  N  L  A  L  I  I  I  L
                                                                    420
       *         *         *         *         *         *         *
AACAAAAGGAGATGAGAAATGTTACCAACATCCTGATTGTGAACCTTTCCTTCTCAGACTTGCTTGTTGC
  K  Q  K  E  M  R  N  V  T  N  I  L  I  V  N  L  S  F  S  D  L  L  V  A
                                                                    490
       *         *         *         *         *         *         *
CATCATGTGTCTCCCCTTTACATTTGTCTACACATTAATGGACCACTGGGTCTTTGGTGAGGCGATGTGT
  I  M  C  L  P  F  T  F  V  Y  T  L  M  D  H  W  V  F  G  E  A  M  C
                                                                    560
       *         *         *         *         *         *         *
AAGTTGAATCCTTTTGTGCAATGTGTTTCAATCACTGTGTCCATTTTCTCTCTGGTTCTCATTGCTGTGG
  K  L  N  P  F  V  Q  C  V  S  I  T  V  S  I  F  S  L  V  L  I  A  V
                                                                    630
       *         *         *         *         *         *         *
AACGACATCAGCTGATAATCAACCCTCGAGGGTGGAGACCAAATAATAGACATGCTTATGTAGGTATTGC
  E  R  H  Q  L  I  I  N  P  R  G  W  R  P  N  N  R  H  A  Y  V  G  I  A
                                                                    700
       *         *         *         *         *         *         *
TGTGATTTGGGTCCTTGCTGTGGCTTCTTCTTTGCCTTTCCTGATCTACCAAGTAATGACTGATGAGCCG
  V  I  W  V  L  A  V  A  S  S  L  P  F  L  I  Y  Q  V  M  T  D  E  P
                                                                    770
       *         *         *         *         *         *         *
TTCCAAAATGTAACACTTGATGCGTACAAAGACAAATACGTGTGCTTTGATCAATTTCCATCGGACTCTC
  F  Q  N  V  T  L  D  A  Y  K  D  K  Y  V  C  F  D  Q  F  P  S  D  S
                                                                    840
       *         *         *         *         *         *         *
ATAGGTTGTCTTATACCACTCTCCTCTTGGTGCTGCAGTATTTTGGTCCACTTTGTTTTATATTTATTTG
  H  R  L  S  Y  T  T  L  L  L  V  L  Q  Y  F  G  P  L  C  F  I  F  I  C
                                                                    910
       *         *         *         *         *         *         *
CTACTTCAAGATATATATACGCCTAA AAAGGAGAAACAACATGATGGACAAGATGAGAGACAATAAGTAC
  Y  F  K  I  Y  I  R  L  K  R  R  N  N  M  M  D  K  M  R  D  N  K  Y
                                                                    980
       *         *         *         *         *         *         *
AGGTCCAGTGAAACCAAAAGAATCAATATCATGCTGCTCTCCATTGTGGTAGCATTTGCAGTCTGCTGGC
  R  S  S  E  T  K  R  I  N  I  M  L  L  S  I  V  V  A  F  A  V  C  W
                                                                   1050
       *         *         *         *         *         *         *
TCCCTCTTACCATCTTTAACACTGTGTTTGATTGGAATCATCAGATCATTGCTACCTGCAACCACAATCT
  L  P  L  T  I  F  N  T  V  F  D  W  N  H  Q  I  I  A  T  C  N  H  N  L
                                                                   1120
       *         *         *         *         *         *         *
GTTATTCCTGCTCTGCCACCTCACAGCAATGATATCCACTTGTGTCAACCCCATATTTTATGGGTTCCTG
  L  F  L  L  C  H  L  T  A  M  I  S  T  C  V  N  P  I  F  Y  G  F  L
                                                                   1190
       *         *         *         *         *         *         *
AACAAAAACTTCCAGAGAGACTTGCAGTTCTTCTTCAACTTTTGTGATTTCCGGTCTCGGGATGATGATT
  N  K  N  F  Q  R  D  L  Q  F  F  F  N  F  C  D  F  R  S  R  D  D  D
                                                                   1260
       *         *         *         *         *         *         *
ATGAAACAATAGCCATGTCCACGATGCACACAGATGTTTCCAAAACTTCTTTGAAGCAAGCAAGCCCAGT
  Y  E  T  I  A  M  S  T  M  H  T  D  V  S  K  T  S  L  K  Q  A  S  P  V
                                                                   1330
       *         *         *         *         *         *         *
CGCATTTAAAAAAAATCAACAACAATGATGATAATGAAAAAATCTGAAACTACTTATAGCCTATGGTCCCG
  A  F  K  K  I  N  N  N  D  D  N  E  K  I  *
```

TABLE 1-continued

Human Neuropeptide Y Y1 receptor cDNA (SEQ ID NO: 3)

```
                                                                                   1400
GATGACATCTGTTTAAAAACAAGCACAACCTGCAACATACTTTGATTACCTGTTCTCCCAAGGAATGGGG
                                                                                   1470
TTGAAATCATTTGAAAATGACTAAGATTTTCTTGTCTTGCTTTTTACTGCTTTTGTTGTAGTTGTCATAA
                                                                                   1540
TTACATTTGGAACAAAAGGTGTGGGCTTTGGGGTCTTCTGGAAATAGTTTTGACCAGACATCTTTGAAGT
                                                                                   1610
GCTTTTTGTGAATTTATGCATATAATATAAAGACTTTTATACTGTACTTATTGGAATGAAATTTCTTTAA
                                                                                   1680
AGTATTACGATNNNCTGACTTCAGAAGTACCTGCCATCCAATACGGTCATTAGATTGGGTCATCTTGATT
                                                                                   1750
AGATTAGATTAGATTAGATTGTCAACAGATTGGGCCATCCTTACTTTATGATAGGCATCATTTTAGTGTG
                                                                                   1820
TTACAATAGTAACAGTATGCAAAAGCAGCATTCAGGAGCCGAAAGATAGTCTTGAAGTCATTCAGAAGTG
                                                                                   1890
GTTTGAGGTTTCTGTTTTTTGGTGGTTTTTGTTTGTTTTTTTTTTTTTCACCTTAAGGGAGGCTTTCAT
                                                                                   1960
TTCCTCCCGACTGATTGTCACTTAAATCAAAATTTAAAAATGAATAAAAAGACATACTTCTCAGCTGCAA
                                                                                   2030
ATATTATGGAGAATTGGGCACCCACAGGAATGAAGAGAGAAAGCAGCTCCCCAACTTCAAAACCATTTTG
                                                                                   2100
GTACCTGACAACAAGAGCATTTTAGAGTAATTAATTTAATAAAGTAAATTAGTATTGCTGCAAATAGCTA
                                                                                   2170
AATTATATTTATTTGAATTGATGGTCAAGAGATTTTCCATTTTTTTTACAGACTGTTCAGTGTTTGTCAA
                                                                                   2240
GCTTCTGGTCTAATATGTACTCGAAAGACTTTCCGCTTACAATTTGTAGAAACACAAATATCGTTTTCCA
                                                                                   2310
TACAGCAGTGCCTATATAGTGACTGATTTTAACTTTCAATGTCCATCTTTCAAAGGAAGTAACACCAAGG
                                                                                   2380
TACAATGTTAAAGGAATATTCACTTTACCTAGCAGGGAAAAATACACAAAAACTGCAGATACTTCATATA
                                                                                   2450
GCCCATTTTAACTTGTATAAACTGTGTGACTTGTGGCGTCTTATAAATAATGCACTGTAAAGATTACTGA
                                                                                   2520
ATAGTTGTGTCATGTTAATGTGCCTAATTTCATGTATCTTGTAATCATGATTGAGCCTCAGAATCATTTG
                                                                                   2590
GAGAAACTATATTTTAAAGAACAAGACATACTTCAATGTATTATACAGATAAAGTATTACATGTGTTTGA

TTTTAAAAGGGCGGACATTTTATTAAAATCAAGG
``` phosphate transfection method. Stably transfected cells were selected with neomycin and tested for the ability to bind NPY/PYY peptide analogues. Transfected cells ($1\times10^6$) were incubated in 0.5 ml assay buffer (50 mM Tris-HCl pH 7.4, 2 mM $CaCl_2$, 5 mM KCl, 120 mM NaCl, 1 mM $MgCl_2$, and 0.1% bovine serum albumin) in the presence of 0.05 nM [$^{125}$I]-labelled peptide YY(NEN) and either $10^{-8}$M porcine peptide YY(PYY 13-36), or the Y1 receptor-selective NPY(Leu31,Pro34) [peptides were obtained from Auspep, Australia]. Peptide analogues were also tested on human neuroblastoma SK-N-MC cells ($1.6\times10^6$), which express only the Y1 receptor subtype, and on rat brain membrane preparations (approximately 100 μg) which express predominantly Y2 receptors. Untransfected CHO K1 cells (1×10⁶) were also tested and showed no specific binding to the peptide analogues. Cells were incubated with the radiolabelled peptide and unlabelled competitors for one hour at room temperature and pelleted in a microcentrifuge for 4 minutes. Pellets were counted for one minute in a gamma counter. Binding of the Y1 receptor-selective agonist confirmed the identify of this clone as the NPY-Y1 receptor.

The expressed NPY Y1 receptor was assessed for its ability to bind NPY and related analogs (methods detailed in human NPY Y1 receptor patent application) (FIG. 1).

The receptor has been successfully used to show specific binding to a Y1receptor-specific agonist NPY ($L^{31}, P^{34}$) and to not bind to a Y2 receptor-specific agonist peptide YY 13–36. These results reflect the in vivo effects of these agonists.

Figure 2:
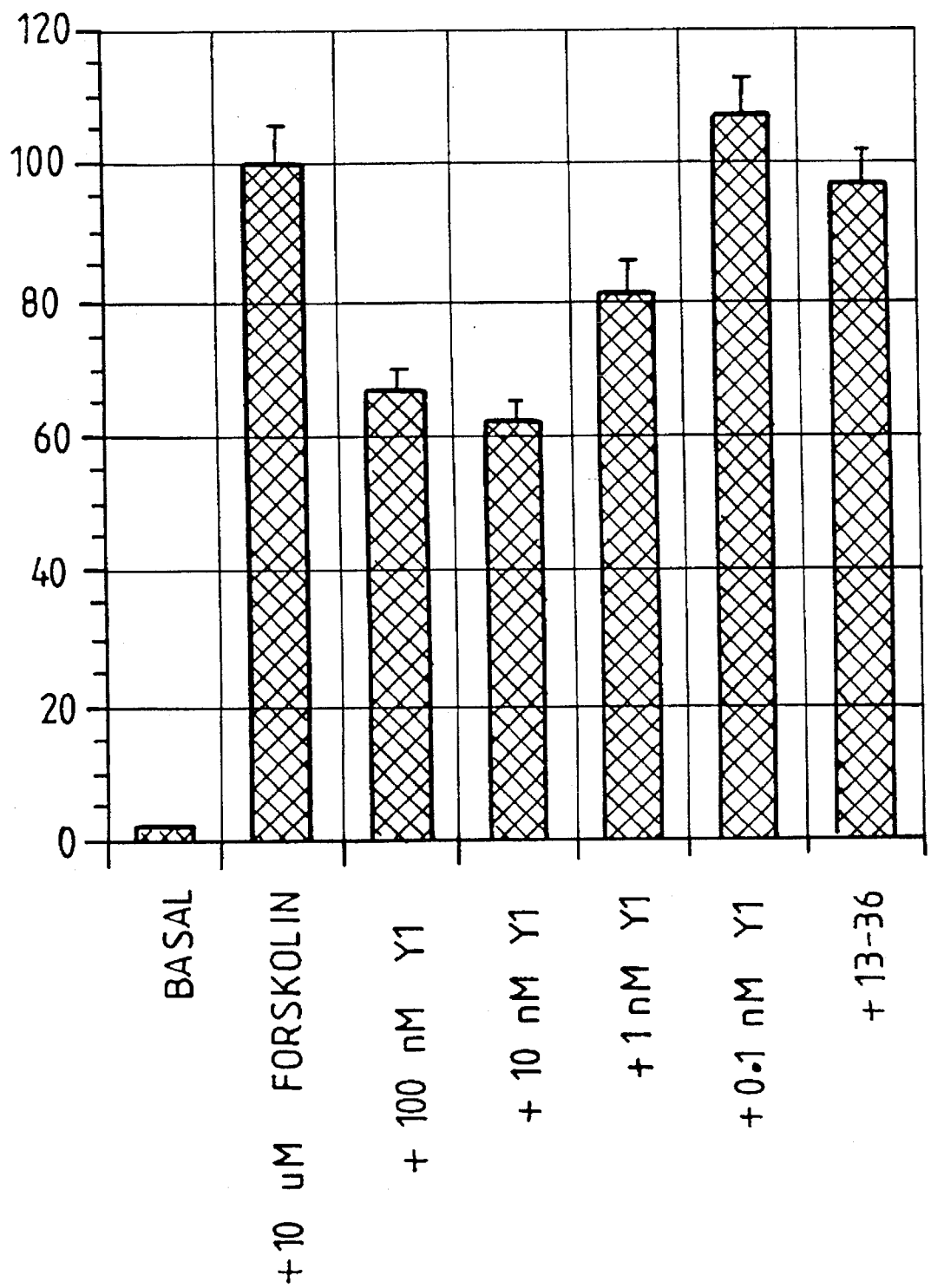
FIG. 2 shows the cyclic AMP response, in 293 cells transfected with human NPY Y1 receptor, to NPY ($L^{31},P^{34}$) (Y1) or porcine PYY-(13–36) is expressed as a percentage of the cyclic AMP level produced with 10 micromolar forskolin from three independent experiments. Basal levels were 2.5+0.13 pmol per $10^6$ cells (untransfected 293 cells) and 2.26+0.06 pmol per $10^6$ cells (transfected 293 cells). Cyclic AMP levels stimulated by 10 micromolar forskolin were 121.2+19.8 pmol per $10^6$ cells (untransfected 293 cells) and 139+14.2 pmol per $10^6$ cells (transfected 293 cells).
Figure 3A:
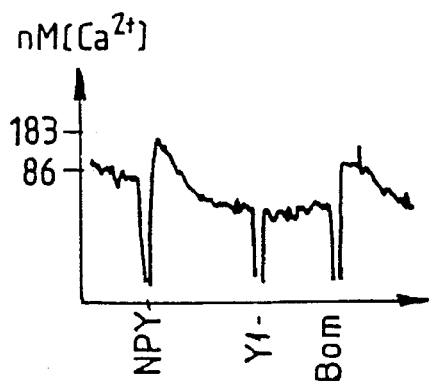
FIG. 3 shows intracellular calcium levels of fura-2-loaded CHO cells transfected with the human NPY Y1 receptor cDNA were measured in response to NPY, NPY ($L^{31},P^{34}$) (Y1), PYY, PYY 13–36, or PP. After successive addition of two of these compounds the intracellular calcium response mediated by the endogenous bombesin receptor was measured with the addition of 1 micromolar bombesin (Bom). The NPY Y1 receptor expressing cell line was stimulated with 100 nM NPY(A), peptide YY (B), NPY (L,P) (C), peptide YY cells did not respond to any of the NPY analogues, including 100 nM NPY ($L^{31},P^{34}$) (F). Treatment of stably transfected cells overnight with pertussis toxin at 100 ng.ml abolished the response to 2.5 micromolar PYY (H), as compared with untreated cells (G), but did not affect the intracellular response to 1 micromolar bombesin. The intracellular calcium increase mediated by the NPY Y1 receptor was dependent on the concentration of NPY ($L^{31}$, $P^{34}$) and was maximal at 10 nM (J).
Figure 3D:
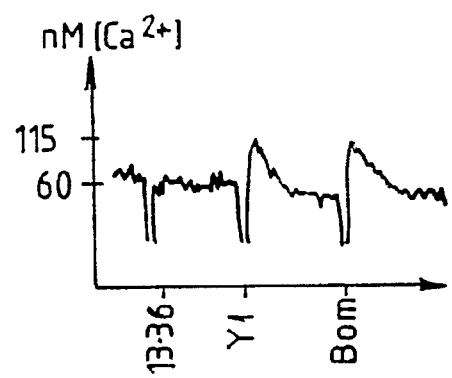
Figure 3B:
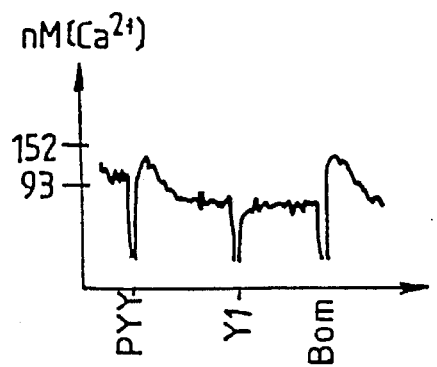
Figure 3E:
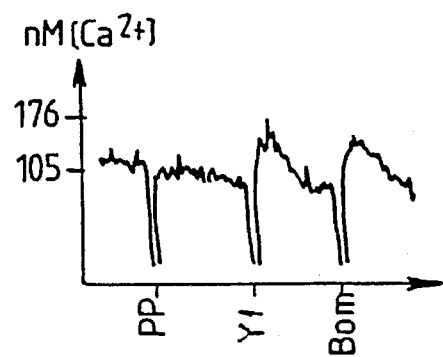
Figure 3C:
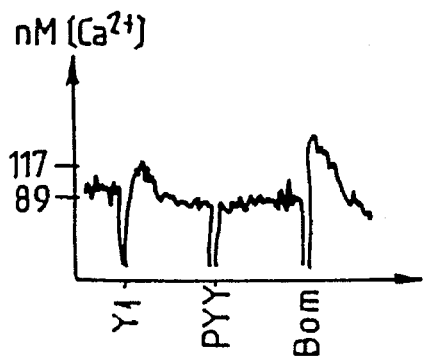
Figure 3F:
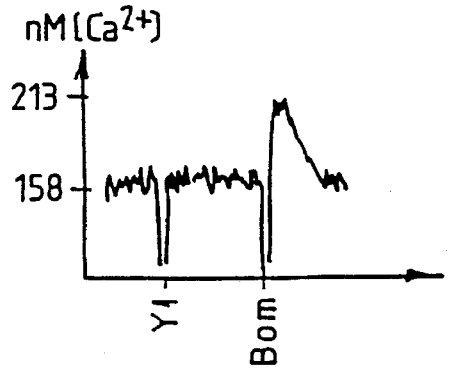
Figure 3G:
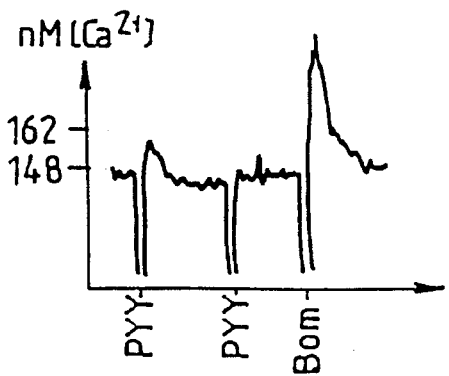
Figure 3H:
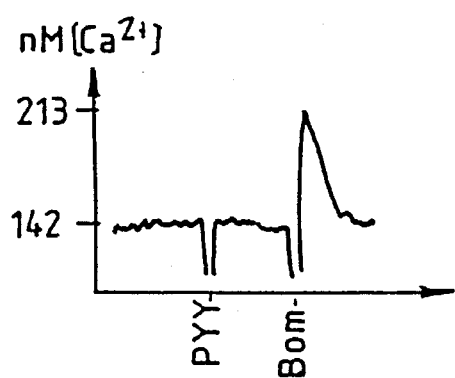
Figure 3J:
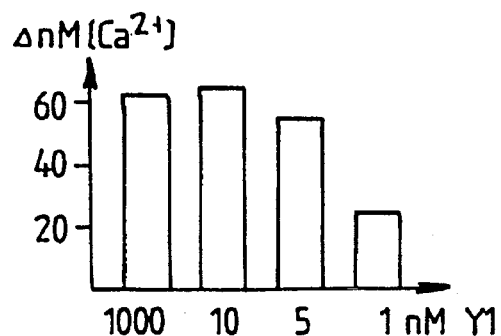

In the present invention, the Y1receptor expressed in these cell lines has been shown to couple to inhibition of adenylate cyclase in 293 cells (FIG. 2) and the increase in cytosolic calcium levels in the CHO cells (FIG. 3). These are significant and novel findings and of use in the screening of agonists and antagonists by function.

To measure intracellular cyclic AMP levels, cyclic AMP was assayed in whole cells treated for 15 min. at 37° C. with 100 micromolar isobutylmethylxanthine (IBMX; Sigma). Transfected cells (1×10⁶/0.5 ml reaction) were incubated with 10 micromolar forskolin and various concentrations of NPY and related peptides. Reactions were terminated with the addition of HCl to 0.1M, incubation at room temperature for 15 min., neutralisation and sample dilution in 50 mM sodium acetate, pH 6.2. Cyclic AMP was quantitated by using a radioimmunoassay (Dupont/NEN).

To measure levels of intracellular calcium, transfected cells were suspended in loading medium (modified RPMI 1640 medium/10 mM Hepes/1% newborn calf serum) and incubated in a spinner flask at 37° C. for 2.5 hour at 1×10⁶ cells per ml. Cells were then treated with 1 micromolar Fura-2 acetoxymethyl ester (fura-2 AM; Molecular Probes) for 30 min. at 37° C., washed twice with loading medium, and resuspended at 5×10⁶ cells/ml. Immediately before fluorescence spectroscopy, cells were recovered by centrifugation at 1000 rpm and resuspended at 1×10 cells/ml in a modified Krebs buffer (135 mM NaCl/ 4.7 mM KCl/1.2 mM $MgSO_4$/1.2 mM $KH_2PO_4$/5 mM $NaHCO_3$/1 mM $CaCl_2$/2.8 mM glucose/10 mM Hepes, pH 7.4) containing sulfinpyrazone. Bombesin was purchased from Sigma and Auspep. Fluorescence recordings were made on a Hitachi fluorescence spectrometer (F4010) at 340 nm (excitation) and 505 nm (emission) over 10 min. with slit widths of 5 nm and response time of 2 seconds. Intracellular calcium was quantitated by using equations described by Grynkiewicz, et al., J. Bio. Chem. 260:3440–3450, 1985.

Plasmid Construction

Plasmid pMalp (Promega), which carries the malE gene under the control of the tac promoter, was cut with EcoRI and HindII restriction enzymes simultaneously. A 2.1 kb EcoRI/HindIII cDNA fragment containing the whole coding region for the human NPY Y1 receptor was cloned into the pMalp vector to generate plasmid pHz59. The plasmid pHz59 was cut with StuI and EcoRI restriction enzymes simultaneously and the 5' overhang of the EcoRI site was filled in with Klenow enzyme and the plasmid was religated to generate the fusion construct pHz60. The recombinant plasmid (pHz60) was transfected into the bacterial strain TB1.

Preparation and Fractionation of E. coli Membranes

Bacteria were grown at 37° C. in L broth containing 501 g/ml of ampicillin, up to an A600 value of 0.5–0.7. Derepression of the tac promoter with 1 mM isopropylb-D-thiogalactopyranoside (IPTG) for 2 hours at 37 C let to the production of a 86 kD malE/NPY Y1 receptor fusion-protein. Cells, from a 1 l culture, were harvested and washed at 4° C. with 1 l 10 mM Hepes pH 7.5 and the pellet stored over night at −20° C. All the subsequent steps were carried out on ice. The bacterial pellet was suspended in 28 ml 10 mM Hepes pH 7.5 containing 20% (by mass) sucrose, DNAse I at 30 lg/ml, and RNase A at 30 lg/ml, and the following protease inhibitors: 1 mM phenylmethylsulfonylfluoride, leupeptin at 1 lg/ml, and pepstatin at 7 lg/ml. The suspension was sonicated three times for 3 min. Unbroken cells were removed by centrifugation at 5000 g for 10 min. and 2 ml 0.1M EDTA (pH 7.5) was added to the supernatant. This supernatant was layered on a sucrose gradient consisting of 3 ml 60% (mass/vol.) sucrose, 6 ml 42.5% (mass/vol.) sucrose, and 15 ml 25% (mass/vol.) sucrose (in 10 mM Hepes pH 7.5 containing 5 mM EDTA) and centrifuged at 100000 g for 16 h at 4° C. in a Beckmann SW41 rotor. Two major bands were visible at the interface of the sucrose layers, corresponding to the enriched preparations of the outer and inner membrane. Fractions were collected from the gradient and aliquots used to measure binding activity for $^{125}I$ NPY, in the biding assay described.

Isolation of the Human NPY Y1 Receptor Gene

A human genomic DNA library constructed in lambda GEM 11 phage vector (Clontec) was screened with a $^{32}P$-labelled cloned NPY Y1 receptor cDNA (nucleotides 14 to 2327) isolated from human hippocampal cDNA. Two positive clones were obtained from 7.5×10⁵ bacteriophage plaques. Clone kC contained an insert of approximately 14 kb and clone kD contained an insert of approximately 11 kb. The insert in kD was subsequently shown to be completely contained within the longer clone. The restriction map for Sac I, Xho I, BamH I and EcoR I of the kC clone is shown in FIG. 4 and sequence set out in Table 2. The insert of this clone was digested with different enzymes and the fragments subcloned into the Bluescript SK vector for sequencing. The exon sequence of the NPY Y1 receptor gene is identical to that of the human hippocampal cDNA described above. The human NPY Y1 receptor gene consists of 3 exons. This is in contrast to many of the other G protein coupled receptor genes, which are intronless. The overall sequence of the gene consists of approximately 10 kb (FIG. 4). The first 57 nucleotides of the 5' untranslated sequence of the human hippocampal NPY Y1 receptor mRNA are separated by a 6 kb intron from the second exon. The second intron (97 bp), containing an in frame stop codon, is located exactly after the proposed fifth transmembrane domain at nucleotide 908 corresponding to the cDNA sequence (Table 2). Introns in several other G-coupled receptor genes (human substance K, human rhodopsin), tend to be positioned the same way, shortly

TABLE 2

(SEQ ID NO:5)

```
AACGTACTCGTGTACATTCTATTTTTTTCTTCATAATGTTCAGTACTGTAGTACTAATCACCGAGAAAAT

TGCATTGACTCTTTTCGACCACCAGGGAAATATTCAGCTCATGGTTCTCCCCAAAAAAACTAAAAAGCAG

CTAAGCGCTGGGAACAAATCTGACTTATTGCATTTTCTCAGTGGGCCAAAGAAAGGAGGGCCGATTGACT

GCTTTGACTTTTTAAAGGTCTTCTCTTTGTTCACTTATAAAGTGAGGAAAACAAATTCTCGGCACTGGCG

TGAGAGTTGAGCGTCACAAAAGAAAGCAAAAGAAAATATTAGTGCCATTATTGTGGCGAATTTCATGTTT
                 AP2
CCCA|GCGAGCCC|TTTGATTCCTGGTTTGGGCTGGCGCTCGAGCTCTCCAGCCGGGTATGACTTCGGCCAC

AAGATGGCACTGACCTGCAAACAAAGAAAAGCACAGTGGCACCGACTTTTTCAAGCCTCGGGAAACTGCC

CTGCCTTCCCCGGAGTCGAGGACTGTGGGGATTAGGGCTTCCTTTCCCTGCGCGGGAGGTCTGTGTCGA

ATAATGTGTGGCTTCTGTTGGATTGCTTTTCTTTCCAAAATTCCTAGGCAATGCTTCCCCGAGGTGTGCA
                                                            CRE
CCTTTGTGAGGTGTTTGTGGGGTTGGGGGAGCTTCAGGCGCTACTCGCGGGA|CGACGTCA|CGTGATCCGG
                                              CAAT
GATGAGGTGGAGTTCGGCTTTAAGGAGGCGTCTCTTCCTAGCTTCA|TCAATCT|TTAGGATCTGAGCAGGA
 TATA                             +1
G|AAATAC|CAGCGGATCTTCCCCACTCTGCTCCCTTCCATTCCCACCCTTCCTTCTTTAATAAGCAGGAGC
                +57
GAAAAAGACAAATTCCAAAGAGGGTAAGTTGCGAGTTTATGCCTTTCCAGAGACTTCTGCGAAATCTCTC

ATTGACAAGGTGAAGGATGAGAGGGGAAGAAAAACGATGCGAGTGTCCGAAACTGGCTCTGGGGGACCAA

GGTGGGGTCTCCAGTGCAGGCAGGTCGCAGGTTGCTCCAAATCACCGGACCGTTCGCGGGCTCCTGCCGA

AGGGTATGGGGACGACGCGGGTGAAAGGAGAGGGTACCCTACGCGGAGTTCGGGCTTTCCCCCCACCTGC

TCCCGGGGAATTTCTGGATGGGGATCCAAGTTTTCCTTTACCCCGGTTCTCTTTAAAAGGCCGAGGCACT

GGGAAGGCGCCCGAGTTCGCCTATCCCACACCCGCTCATTTTCCTTACGTGTCTTGAGCTGGCTGGAGGC

ACTGGCTCTGGCCGCACCGGAGTTTTCGCGGAGTAACTGGCTGGGATGAGCCGGAGAAGGGTGGGCTTGC

ACGTCGCCCAGCGTCGCACGGGTCCGCGGCAGGTGTCGGGCTGGGAGCTGGCGGAGGTGGGAGTAGCCCT

CGGCGCGGACCCCAGCGCGCAAGCCCACCCCCACTTGCGGGTTCCGCGCTTCTCGGCTGCAATCGAGCCG

CGCACCGCAGTACCGGGCGCTTCGAGTGTGGCGCTGCGCCCCGATAGACACCCGAAGCTTTTAATCATCG

GAGTTCTAATCAGGGTTCTCTTTAGCTCTTTCTTTTAGAAAAGTAATGATGGAACGTGGCTGG-------

----------------------------- 6 kb -----------------------------

---------TATTCCTTACTAACTTATAGACCATTATGTTTTACTAAGACTTGTTCTGTAAGCAAGTCC

AATTAAAAATTTTATTTTTTCTTTATTCAGTATGTTTTCACCATTTCTGCTATTTTAGAAAGATGTTTAC
```

TABLE 2-continued (SEQ ID NO:5)

```
AAGATTACATTTTGTTTATTTATTTCAGTGTTTTCACTTTAAAGAGTTCTGTGAGTCAGAAGTCATTTTG

+58
ACTGCCCTCAATAAAATTAGTAATGCAATTGGTCATTTTCTCTTTACAGATTGTTCAGTTCAAGGGAATG

AAGAATTCAGAATAATTTTGGTAAATGGATTCCAATATCGGGAATAAGAATAAGCTGAACAGTTGACCTG

CTTTGAAGAAACATACTGTCCATTTGTCTAAAATAATCTATAACAACCAAACCAATCAAAATGAATTCAA
                                                                M  N  S

CATTATTTTCCCAGGTTGAAAATCATTCAGTCCACTCTAATTTCTCAGAGAAGAATGCCCAGCTTCTGGC
 T  L  F  S  Q  V  E  N  H  S  V  H  S  N  F  S  E  K  N  A  Q  L  L  A

TTTTGAAAATGATGATTGTCATCTGCCCTTGGCCATGATATTTACCTTAGCTCTTGCTTATGGAGCTGTG
 F  E  N  D  D  C  H  L  P  L  A  M  I  F  T  L  A  L  A  Y  G  A  V

ATCATTCTTGGTGTCTCTGGAAACCTGGCCTTGATCATAATCATCTTGAAACAAAAGGAGATGAGAAATG
 I  I  L  G  V  S  G  N  L  A  L  I  I  I  L  K  Q  K  E  M  R  N

TTACCAACATCCTGATTGTGAACCTTTCCTTCTCAGACTTGCTTGTTGCCATCATGTGTCTCCCCTTTAC
 V  T  N  I  L  I  V  N  L  S  F  S  D  L  L  V  A  I  M  C  L  P  F  T

ATTTGTCTACACATTAATGGACCACTGGGTCTTTGGTGAGGCGATGTGTAAGTTGAATCCTTTTGTGCAA
 F  V  Y  T  L  M  D  H  W  V  F  G  E  A  M  C  K  L  N  P  F  V  Q

TGTGTTTCAATCACTGTGTCCATTTTCTCTCTGGTTCTCATTGCTGTGGAACGACATCAGCTGATAATCA
 C  V  S  I  T  V  S  I  F  S  L  V  L  I  A  V  E  R  H  Q  L  I  I

ACCCTCGAGGGTGGAGACCAAATAATAGACATGCTTATGTAGGTATTGCTGTGATTTGGGTCCTTGCTGT
 N  P  R  G  W  R  P  N  N  R  H  A  Y  V  G  I  A  V  I  W  V  L  A  V

GGCTTCTTCTTTGCCTTTCCTGATCTACCAAGTAATGACTGATGAGCCGTTCCAAAATGTAACACTTGAT
    A  S  S  L  P  F  L  I  Y  Q  V  M  T  D  E  P  F  Q  N  V  T  L  D

GCGTACAAAGACAAATACGTGTGCTTTGATCAATTTCCATCGGACTCTCATAGGTTGTCTTATACCACTC
 A  Y  K  D  K  Y  V  C  F  D  Q  F  P  S  D  S  H  R  L  S  Y  T  T

+908
TCCTCTTGGTGCTGCAGTATTTTGGTCCACTTTGTTTTATATTTATTTGCTACTTCAAGGTAAGAAAACT
 L  L  L  V  L  Q  Y  F  G  P  L  C  F  I  F  I  C  Y  F  K

TTTTTTCTATCATTTCCATTTTTACCTTCTTTACACAGAATTCCTCATCAAATGAGTGTTTCTATTTAAA

+909
CTTTTTTCTTCCATAGATATATATACGCCTAAAAAGGAGAAACAACATGATGGACAAGATGAGAGACAAT
              I  Y  I  R  L  K  R  R  N  N  M  M  D  K  M  R  D  N

AAGTACAGGTCCAGTGAAACCAAAAGAATCAATATCATGCTGCTCTCCATTGTGGTAGCATTTGCAGTCT
 K  Y  R  S  S  E  T  K  R  I  N  I  M  L  L  S  I  V  V  A  F  A  V

GCTGGCTCCCTCTTACCATCTTTAACACTGTGTTTGATTGGAATCATCAGATCATTGCTACCTGCAACCA
 C  W  L  P  L  T  I  F  N  T  V  F  D  W  N  H  Q  I  I  A  T  C  N  H

CAATCTGTTATTCCTGCTCTGCCACCTCACAGCAATGATATCCACTTGTGTCAACCCCATATTTTATGGG
 N  L  L  F  L  L  C  H  L  T  A  M  I  S  T  C  V  N  P  I  F  Y  G

TTCCTGAACAAAAACTTCCAGAGAGACTTGCAGTTCTTCTTCAACTTTTGTGATTTCCGGTCTCGGGATG
 F  L  N  K  N  F  Q  R  D  L  Q  F  F  F  N  F  C  D  F  R  S  R  D

ATGATTATGAAACAATAGCCATGTCCACGATGCACACAGATGTTTCCAAAACTTCTTTGAAGCAAGCAAG
 D  D  Y  E  T  I  A  M  S  T  M  H  T  D  V  S  K  T  S  L  K  Q  A  S
```

TABLE 2-continued (SEQ ID NO:5)

```
CCCAGTCGCATTTAAAAAAATCAACAACAATGATGATAATGAAAAAATCTGAAACTACTTATAGCCTATG
  P   V   A   F   K   K   I   N   N   N   D   D   N   E   K   I   *

GTCCCGGATGACATCTGTTTAAAAACAAGCACAACCTGCAACATACTTTGATTACCTGTTCTCCCAAGGA

ATGGGGTTGAAATCATTTGAAAATGACTAAGATTTTCTTGTCTTGCTTTTTACTGCTTTTGTTGTAGTTG

TCATAATTACATTTGGAACAAAAGGTGTGGGCTTTGGGGTCTTCTGGAAATAGTTTTGACCAGACATCTT

TGAAGTGCTTTTTGTGAATTTATGCATATAATATAAAGACTTTTATACTGTACTTATTGGAATGAAATTT

CTTTAAAGTATTACGATNNNCTGACTTCAGAAGTACCTGCCATCCAATACGGTCATTAGATTGGGTCATC

TTGATTAGATTAGATTAGATTAGATTGTCAACAGATTGGGCCATCCTTACTTTATGATAGGCATCATTTT

AGTGTGTTACAATAGTAACAGTATGCAAAAGCAGCATTCAGGAGCCGAAAGATAGTCTTGAAGTCATTCA

GAAGTGGTTTGAGGTTTCTGTTTTTTGGTGGTTTTTGTTTGTTTTTTTTTTTTCACCTTAAGGGAGGC

TTTCATTTCCTCCCGACTGATTGTCACTTAAATCAAAATTTAAAAATGAATAAAAAGACATACTTCTCAG

CTGCAAATATTATGGAGAATTGGGCACCCACAGGAATGAAGAGAGAAAGCAGCTCCCCAACTTCAAAACC

ATTTTGGTACCTGACAACAAGAGCATTTTAGAGTAATTAATTTAATAAAGTAAATTAGTATTGCTGCAAA

TAGCTAAATTATATTTATTTGAATTGATGGTCAAGAGATTTTCCATTTTTTTACAGACTGTTCAGTGTT

TGTCAAGCTTCTGGTCTAATATGTACTCGAAAGACTTTCCGCTTACAATTTGTAGAAACACAAATATCGT

TTTCCATACAGCAGTGCCTATATAGTGACTGATTTTAACTTAATGTCCATCTTTCAAAGGAAGTAACA

CCAAGGTACAATGTTAAAGGAATATTCACTTTACCTAGCAGGGAAAAATACACAAAAACTGCAGATACTT

CATATAGCCCATTTTAACTTGTATAAACTGTGTGACTTGTGGCGTCTTATAAATAATGCACTGTAAAGAT

TACTGAATAGTTGTGTCATGTTAATGTGCCTAATTTCATGTATCTTGTAATCATGATTGAGCCTCAGAAT

CATTTGGAGAAACTATATTTTAAAGAACAAGACATACTTCAATGTATTATACAGATAAAGTATTACATGT

GTTTGATTTTAAAAGGGCGGACATTTTATTAAAATCAAGG
``` after or in front of a transmembrane domain. This organisation is also consistent with suggestions that the following third cytoplasmatic loop of the receptor forms a specific domain involved in determination of the specificity of coupling to different G proteins. The nucleotide sequences of the two introns adjoining the splice junctions (Table 2) are consistent with the recognised consensus sequence GT/AG.

Putative Regulatory Sequence Elements

Identification of the transcriptional initiation site was carried out with primer extension, using a 21mer primer corresponding to nucleotides 38 to 18. The primer when extended on mRNA derived from the NPY Y1 receptor specific expressing human neuroblastoma cell line SK-N-MC, revealed a transcription start site at 210 nucleotides upstream from the initiation start codon. This position is also identical with a type 1 cap site (CCATTC) (SEQ ID NO:6) and is accompanied 35 bp upstream by a TATA box-like motif (AAATAC) (SEQ ID NO:7), a typical CAAT box (TCAATCT) (SEQ ID NO:8) 60 bp upstream, a cAMP response element (CGACGTCA) (SEQ ID NO:9) 124 bp upstream and a AP2 recognition site (GCGAGCCC) (SEQ ID NO:10) 451 bp upstream (Table 2). No other typical transcription factor binding sites are found in the + orientation in this region. A potential polyadenylation site (ATTAAA) (SEQ ID NO:11) was found at position 2670 of the cDNA sequence. The approximate 2.7 kb sequence of the cDNA is consistent with the size of the NPY Y1 receptor mRNA demonstrated in Nothern analysis of placental and kidney mRNA.

Characterisation of a Pst I Polymorphism in the Human NPY Y1 Receptor Gene

Southern blot analysis was performed using the $^{32}$P-labelled cDNA fragment (nucleotides 14 to 2327) as a probe. The restriction patterns obtained with BamH I, EcoR I and Sac I correspond exactly to the fragments found in the human genomic clones. However, the pattern for the restriction enzyme Pst I shows an additional 5.1 kb band, which suggests the presence of a polymorphic site within the first intron of the gene. Southern blot analysis of genomic DNA samples from 69 normal individuals confirmed this suggestion and demonstrated that the allele frequency for the Pst I polymorphism in this population is 54%:46% (Table 3). Sequence analysis revealed a single point mutation in the recognition site for the restriction enzyme Pst I, changing the first cytidine to a thymidine. The polymorphism could be used to assess variations in the population which may represent a possible marker for hypertension.

Genomic Library Screening

A human peripheral blood genomic DNA library (Clontec) was screened with a $^{32}$P-labelled 2.3 kb fragment (nucleotides 14 to 2327) of the human NPY Y1 receptor cDNA. Bacteriophage DNA was transferred to Hybond N$^+$ filters (Amersham) and hybridised with the probe in a solution containing 6×SSC, 5×Denhardt's and 0.1% SDS at 65° C. for 16 h. Filters were washed twice 15 min in 2×SSC/0.1% SDS at 65° C. followed by a 15 min wash in 0.1×SSC/0.1% SDS and exposed to X-ray film (Kodak, X-Omat) using an intensifying screen at −70° C. for 16 h. Positive plaques were purified and DNA was isolated using a standard lysate procedure. kDNA was digested with EcoR I, Hind III, BamH I, Sac I, Xho I, or combinations of these enzymes to generate subsequently ordered subclones in the Bluescript SK vector (Stratagene) covering the entire region of the NPY Y1 receptor gene.

Nucleotide Sequence Determination

Supercoiled plasmid DNA was alkaline-denatured and sequenced by the dideoxy chain termination method using T7 polymerase (Promega). Oligonucleotide primers were initially from the flanking region of the vector and internal to the cDNA sequence. Additional primers were synthesised based on intron sequence obtained.

TABLE 3

NPY Y1 Receptor Gene Pst I Polymorphism

|  | Genoptypes | | | Allele Frequency | |
|---|---|---|---|---|---|
|  | 3.8/3.8 | 3.8/5.1 | 5.1/5.1 | 3.8 | 5.1 |
| Samples (69) | 22 | 30 | 17 | 74 | 64 |
| Frequency | 31.9% | 43.4% | 24.6% | 53.6% | 46.4% |

NOY Agonist and Antagonist Sequesing

The mammalian cells transfected with the human NPY Y1 receptor cDNA were used to identify a peptide antagonist of NPY function.

Using synthetic peptide chemistry, a hexapeptide amide SALRHY-NH$_2$ (Ser-Ala-Leu-Arg-His-Tyr amide) (SEQ ID NO:12), which corresponds to residues 22–27 of the NPY molecule portion of the amphiphatic helix in NPY was synthesised in an ABI Peptide Synthesiser Model 430A. T-boc chemistry was used. HF cleavage was used to release peptide from the solid support. Peptide was subjected to HPLC (Ion Exchange and Reverse Phase) purifications. The peptide was subjected to sequence and amino acid analysis for sequence integrity. In a series of experiments not described here in anaesthetized rates significant inhibition of the NPY-evoked pressor response and a decrease in resting blood pressure levels 60 minutes after administration of SALRHY-NH$_2$ was observed. The inhibitory effect of SAL-RHY-NH$_2$ is confined to the postsynaptic or Y1 receptor as no significant inhibitory effects are seen on attenuation of cardiac vagal action, a Y2receptor mediated function.

The hexapeptide was tested in vitro for its ability to inhibit NPY effects on mammalian cell lines transfected with the human NPY Y1 receptor cDNA. The ability of the hexapeptide to block the NPY-induced increase in intracellular calcium correlated well with its in vivo ability to block NPY Y1 receptor-mediated increases in blood pressure.

Figure 5B:
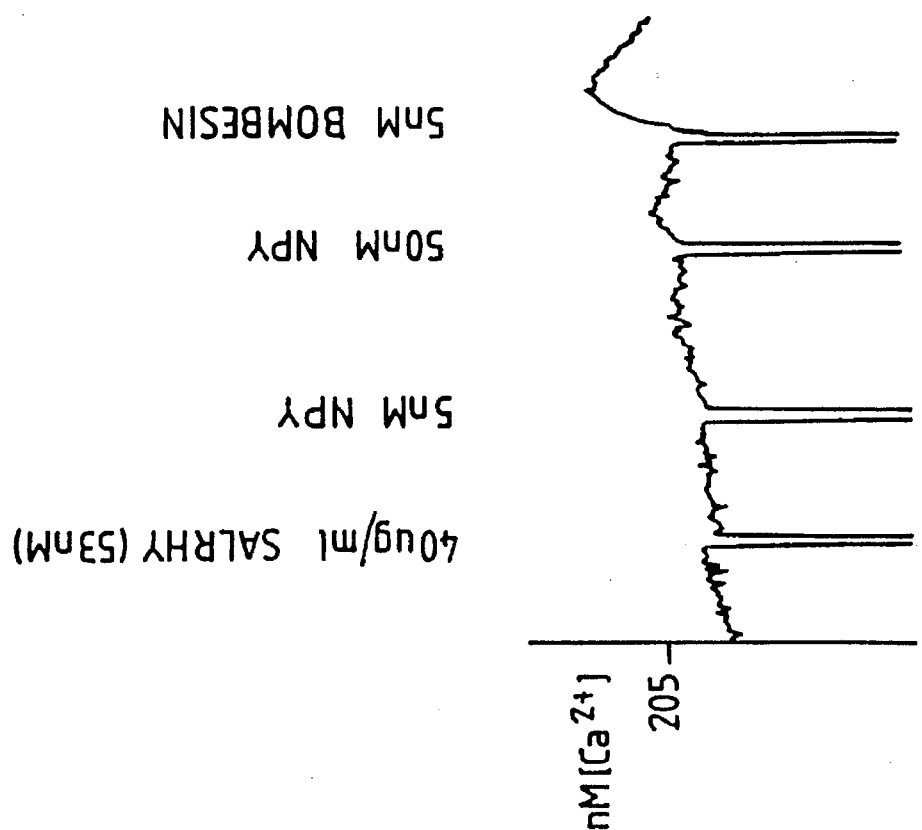
FIG. 5 shows the results obtained when CHO cells expressing human NPY-Y1 receptor were loaded with FURA-2 AM and stimulated with 5 nM or 50 nM human NPY after the addition of 40 μg/ml hexapeptide. Increases in calcium induced by the endogenous bombesin receptor were measured by the addition of 5 nM bombesin.
Figure 5A:
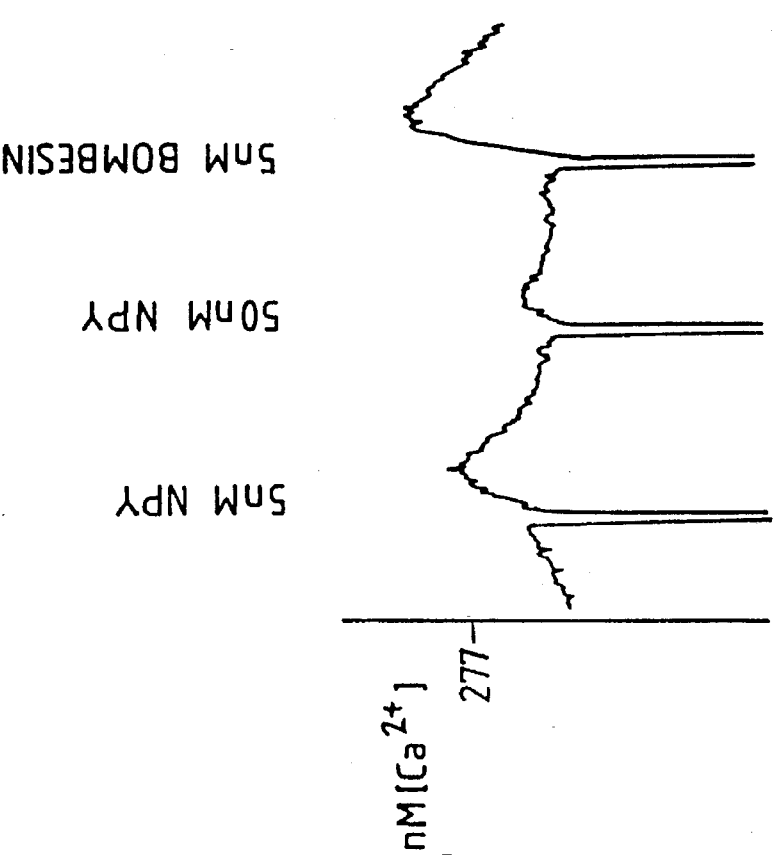

CHO cells expressing the human NPY Y1 receptor were loaded with FURA-2 AM as described, and stimulated with 5 nM or 50 nM human NPY (Auspep) after the addition of 40 lg/ml SALRHY-NH2 hexapeptide. Increases in calcium induced by the endogenous bombesin receptor were measured by the addition of 5 nM bombesin. The results are shown in FIG. 5.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

We claim:

1. A cDNA molecule encoding the human NPY-Y 1 receptor, the cDNA molecule encoding the amino acid sequence shown in SEQ ID NO: 4.

2. A genomic DNA molecule encoding the human NPY-Y1 receptor, the genomic DNA molecule encoding the amino acid sequence shown in SEQ ID NO:4.

3. A method of producing human NPY-Y1 receptors comprising culturing a cell transformed with the cDNA molecule of claim 1 under conditions which allow expression of the DNA sequence and optionally recovering the human NPY-Y1 receptor.

4. A method as claimed in claim 3 in which the method comprises culturing a bacterial cell transformed with the cDNA molecule as claimed in claim 1.

5. A method as claimed in claim 3 in which the cell is a mammalian cell.

6. A method as claimed in claim 5 in which the cell is a Chinese Hamster Ovary cell or human embryonic kidney 293 cell.

7. A method as claimed in claim 3 in which the cDNA molecule is under the control of the CMV promoter.

8. A method of producing human NPY-1 receptors comprising culturing a cell transformed with the genomic DNA molecule of claim 2 under conditions which allow expression of the DNA sequence and optionally recovering the human NPY-Y1 receptor.

9. A method as claimed in claim 8 in which the cell is a mammalian cell.

10. A method as claimed in claim 9 in which the cell is a Chinese hamster ovary cell or human embryonic kidney 293 cell.

* * * * *

UNITED STATES PATENT AND TRADEMARK OFFICE
CERTIFICATE OF CORRECTION

PATENT NO. : 5,571,695
DATED : November 5, 1996
INVENTOR(S) : Lisa Selbie et al.

It is certified that error appears in the above-indentified patent and that said Letters Patent is hereby corrected as shown below:

```
Title page, Item [57], Line 4, "sued" should be -- used --;
                    Col. 3, between lines 24-25, please
 insert the following -- BRIEF DESCRIPTION OF THE DRAWINGS --;
 Col. 3, delete line 30 in its entirety; Col. 9, line 18,
 "Y1receptor" should be -- Y1 receptor --;
                    Col. 32, line 40 (claim 8), "NPY-1" should be --
 NPY-Y1 --.
```

Signed and Sealed this

Twenty-fifth Day of March, 1997

Attest:

BRUCE LEHMAN

*Attesting Officer*     *Commissioner of Patents and Trademarks*